United States Patent
Healey et al.

(10) Patent No.: US 10,028,798 B1
(45) Date of Patent: Jul. 24, 2018

(54) SINGLE-USE DISPOSABLE STERILE KIT

(71) Applicant: DEPUY SYNTHES PRODUCTS, INC., Raynham, MA (US)

(72) Inventors: Richard Healey, West Chester, PA (US); Philip Watt, West Chester, PA (US); Steven Greco, West Chester, PA (US); David Moszak, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/415,624

(22) Filed: Jan. 25, 2017

(51) Int. Cl.
| | |
|---|---|
| *A61B 50/33* | (2016.01) |
| *B65D 25/20* | (2006.01) |
| *A61B 50/00* | (2016.01) |
| *A61B 50/30* | (2016.01) |
| *A61B 17/88* | (2006.01) |

(52) U.S. Cl.
CPC ............ *A61B 50/33* (2016.02); *B65D 25/205* (2013.01); *A61B 17/88* (2013.01); *A61B 2050/0058* (2016.02); *A61B 2050/0084* (2016.02); *A61B 2050/3008* (2016.02)

(58) Field of Classification Search
CPC ......... A61B 17/88; A61B 19/02; A61B 50/33; A61B 2050/0058; A61B 2050/3008; A61B 2050/0084; B65D 25/20; B65D 25/205; B65D 85/00
USPC ......... 206/370, 438, 439, 570–572; 220/324, 220/326
See application file for complete search history.

(56) References Cited

U.S. PATENT DOCUMENTS

| | | | | |
|---|---|---|---|---|
| 4,643,303 | A * | 2/1987 | Arp ........................... | A61L 2/26 206/370 |
| 5,031,768 | A * | 7/1991 | Fischer .................. | A61B 50/31 206/364 |
| 5,311,990 | A * | 5/1994 | Kalinski ................ | B65D 25/04 206/370 |
| 5,690,222 | A | 11/1997 | Peters | |
| 5,881,878 | A | 3/1999 | Faccioli et al. | |
| 6,138,850 | A * | 10/2000 | Berry ........................ | A61L 2/26 206/369 |
| 6,161,695 | A | 12/2000 | Nicolais | |
| 6,365,115 | B1 | 4/2002 | Wood | |
| 6,426,041 | B1 | 7/2002 | Smith | |
| 7,441,668 | B2 * | 10/2008 | O'Malley ............ | A47B 73/004 211/74 |
| 8,685,068 | B2 | 4/2014 | Sixto et al. | |
| 8,911,677 | B2 * | 12/2014 | Gerstner .................. | A61L 2/10 206/370 |
| 9,107,502 | B2 | 8/2015 | Heede et al. | |
| 9,844,417 | B2 * | 12/2017 | Gerstner ................ | A61B 50/33 |
| 2005/0033430 | A1 | 2/2005 | Powers et al. | |
| 2009/0205988 | A1 | 8/2009 | Edwards et al. | |

(Continued)

*Primary Examiner* — Bryon Gehman

(57) ABSTRACT

A single use disposable surgical kit, including a sterile sealed container including a module configured to fit within the sterile sealed container including surgical instruments housed in a bottom tray including a first fastening feature; and a lid including a second fastening feature congruently aligned with the first fastening feature, wherein the first fastening feature is one of a tab portion and a mating slot, the second fastening feature is the other of the tab portion and the mating slot, and the second fastening feature is configured to engage with the first fastening feature.

32 Claims, 12 Drawing Sheets

(56) References Cited

U.S. PATENT DOCUMENTS

2013/0334083 A1* 12/2013 Bugnard ............ A61B 19/0271
206/370
2016/0287901 A1* 10/2016 Dumaine ............. A61N 5/1015

* cited by examiner

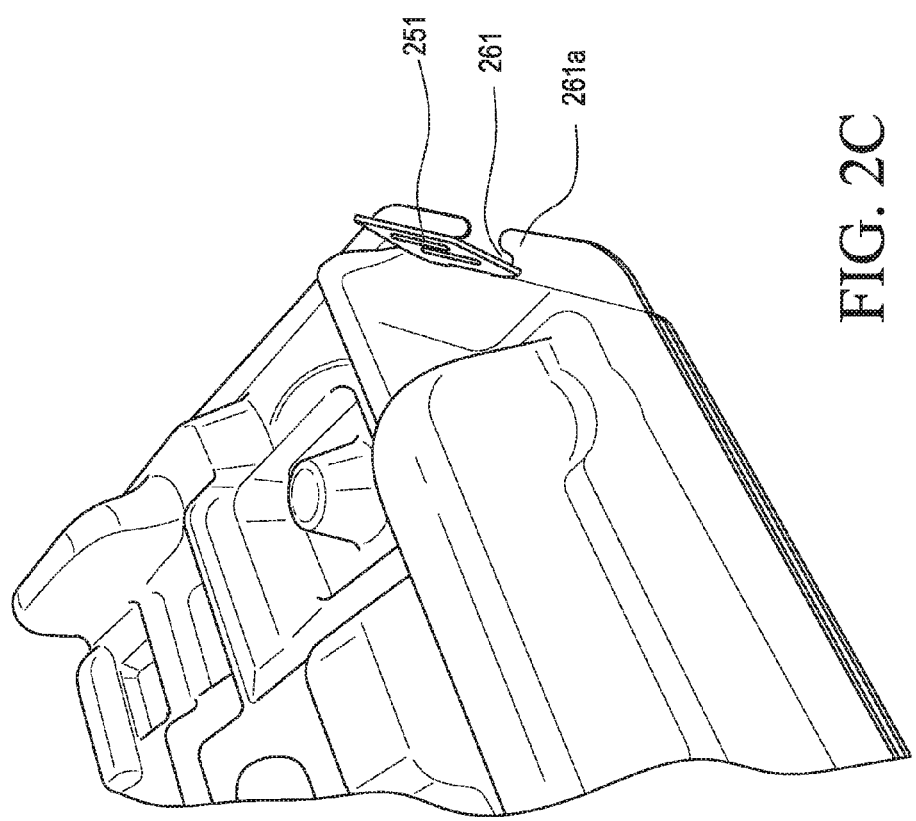

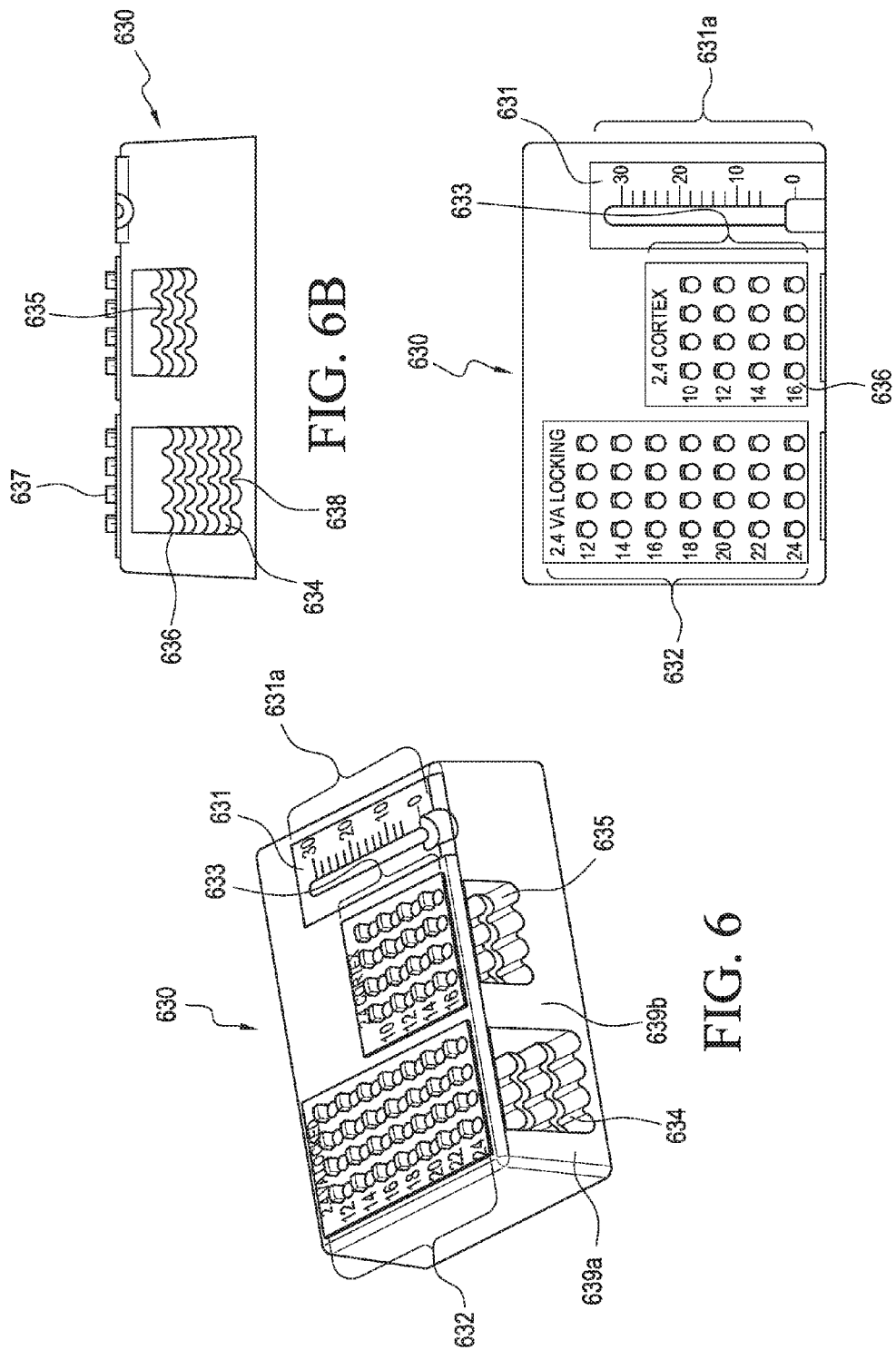

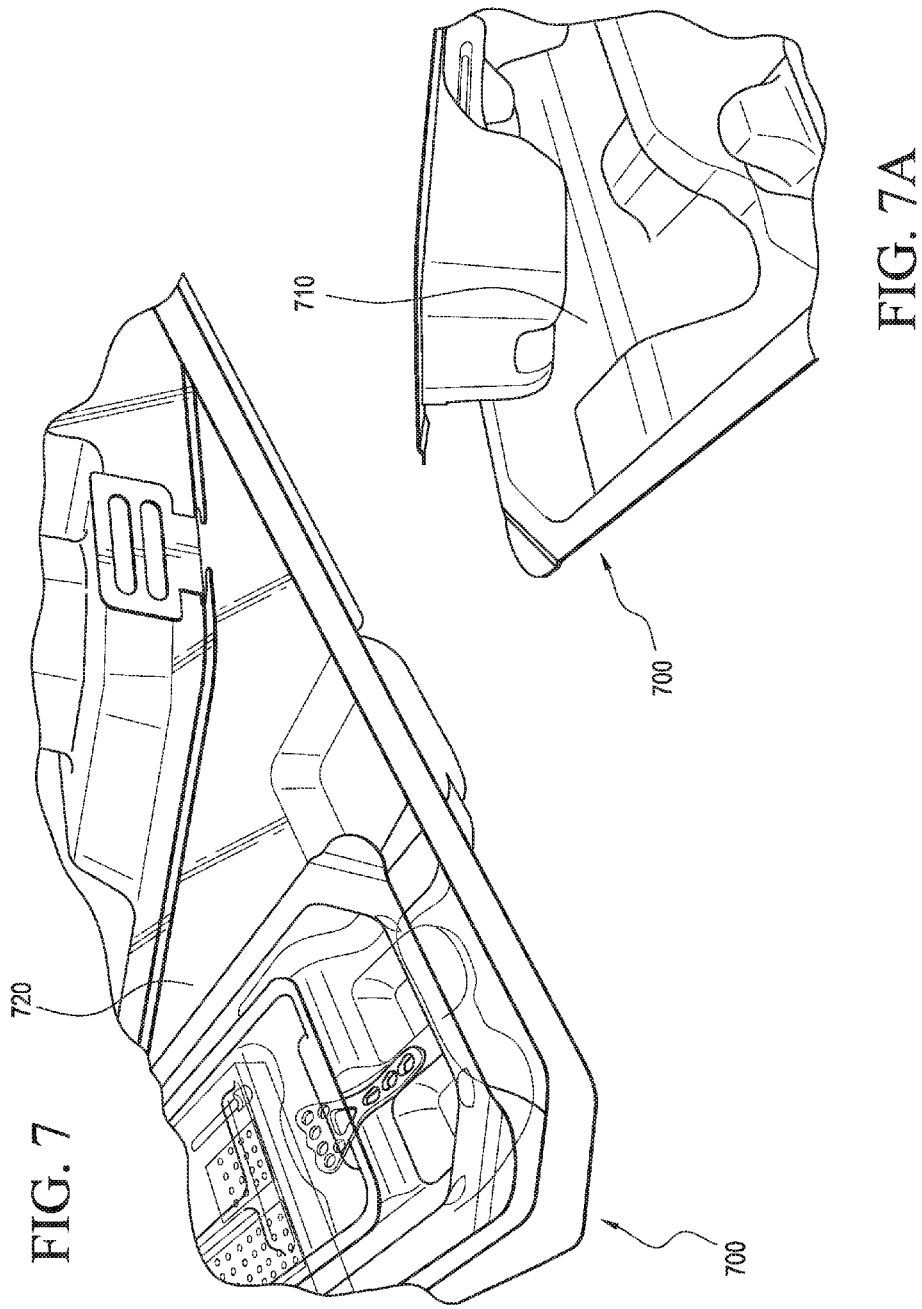

SINGLE-USE DISPOSABLE STERILE KIT

TECHNICAL FIELD

Various exemplary embodiments disclosed herein relate generally to a single-use disposable sterile kit.

BACKGROUND

Conventional surgical kits are typically provided by manufacturers in non-sterile, reusable instrument sets that are too cost-prohibitive for use in smaller healthcare facilities, such as Ambulatory Surgical Centers. Such kits are also problematic for high-volume periods of usage in hospitals due to the need for reprocessing steps which are time and cost dependent.

Disposable orthopedic surgical kits are generally sold as sterile kits that contain bone plate(s) and a plurality of fasteners as well as housings for the fasteners. The kits also may contain wires, drill bits, drill guides, depth gauges and screwdrivers. Disposable kits help provide streamlined, cost-effective instrument sets to a wider range of healthcare facilities.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

This disclosure relates generally to a single-use disposable sterile kit. An example of such a sterile kit is a single-use disposable orthopedic surgical sterile kit that allows for the implantation of bone plates for the fixation of bone fractures. The single-use disposable orthopedic surgical sterile kit will be used as an example sterile kit, but sterile kits for other applications may be carried out according to the disclosure below.

Various embodiments relate to a single-use disposable sterile kit, including a sterile sealed container, a first module including a single bone plate having a plurality of fastener apertures, a fastener housing including a plurality of protrusions, stairs and concave depressions for housing a plurality of fasteners; and a second module including instruments required to fixate a bone fracture. In various embodiments, the first and second modules sit within two separate cutout sections of the sterile sealed container.

Various additional embodiments relate to a single use disposable orthopedic surgical kit including a sterile-sealed container including a first module configured to fit within the sterile sealed container including: a single bone plate including a plurality of fastener apertures and a fastener housing including a plurality of protrusions on the top of the fastener housing, a plurality of stairs extending downward from the top of the fastener housing, and a plurality of concave depressions located on the top surface of the plurality of stairs for housing a plurality of fasteners, each of the plurality of fasteners including a head and a shaft.

Various additional embodiments relate to a single use disposable orthopedic surgical kit including a first module including: a single bone plate including a plurality of fastener apertures and a fastener housing including a plurality of protrusions on the top of the fastener housing, a plurality of stairs extending downward from the top of the fastener housing and a plurality of concave depressions located on the top surface of the plurality of stairs for housing a plurality of fasteners, each of the plurality of fasteners including a head and a shaft. The kit further includes a second module including instruments used to fixate a bone fracture.

Various additional embodiments relate to a single use disposable orthopedic surgical kit including a first module including a single bone plate including a plurality of fastener apertures and a fastener housing including a plurality of protrusions on the top of the fastener housing, a plurality of stairs extending downward from the top of the fastener housing and a plurality of concave depressions located on the top surface of the plurality of stairs for housing a plurality of fasteners, each of the plurality of fasteners including a head and a shaft. In various embodiments of the kit, the plurality of protrusions extend upward and away from the top of the fastener housing and the plurality of concave depressions are integrally formed on the top surface of the plurality of stairs. The kit additionally includes a second module including instruments used to fixate a bone fracture.

Various embodiments relate to a first module including a first well and a second well. In various embodiments, the fastener housing is included in the first well and the bone plate included in the second well.

Various embodiments are described wherein the first module includes a one-shot injection-molded fastener housing having a plurality of protrusions extending upward from the top of the fastener housing and having a plurality of stairs and a plurality of concave depressions included within a first and second cavity of the fastener housing to prevent the fasteners from threading into the fastener housing. In various embodiments, the plurality of concave depressions are integrally formed with the top surface of the stairs. In various embodiments, the plurality of protrusions, plurality of stairs and plurality of concave depressions work together to prevent fastener angulation or jamming during transit and handling.

In various embodiments of the first module, the plurality of fasteners is arranged in the fastener housing in a plurality of groupings of the fasteners. The first one of the plurality of groupings includes only fasteners having a first shaft length and the second one of the plurality of groupings includes only fasteners having a second shaft length that is different from the first shaft length. The fasteners in the first one of the plurality of groupings are segregated from the fasteners in the second one of the plurality of groupings. In various embodiments, the fastener housing may include a first fastener receptacle to house the first one of the plurality of groupings of fasteners and a second fastener receptacle to house the second one of the plurality of groupings of fasteners. In various embodiments, the fasteners sit within the fastener housing in a staggered configuration. The heads of the fasteners are dimensioned to mate with the fastener apertures in the bone plate. In one embodiment, the head and shaft of the fasteners both include threads.

In various embodiments of the first module, the lengths of the fasteners are based on the included bone plate and anatomic study. The fasteners may include a first sized head or a second sized head. All of the fastener apertures of the bone plate may be dimensioned to receive either the first sized head or the second sized head. The kit may include forty-four or fewer fasteners, each of which may have one of seven different shaft lengths. The fasteners may be arranged in the fastener housing in a plurality of groupings of four or fewer fasteners, each having the same shaft length.

Various embodiments are described wherein the fastener housing may include labels to indicate the shaft length of each of the plurality of groupings of fasteners. The fastener housing may include a fastener length gauge to aid the user in determining the length of each of the plurality of fasteners.

Various embodiments of the first module are described wherein the bone plate, fasteners and fastener housing are housed in a double-sterile barrier to ensure sterility.

Various further embodiments relate to a single use disposable surgical kit including a sterile sealed container including: a first module configured to fit within the sterile sealed container including a single bone plate including a plurality of fastener apertures and a fastener housing; and a second module configured to fit within the sterile sealed container including instruments used to fixate a bone fracture housed in a bottom tray including a first fastening feature and a lid including a second fastening feature congruently aligned with the first fastening feature wherein the first fastening feature is one of a tab portion and a mating slot, the second fastening feature is the other of the tab portion and the mating slot and the second fastening feature is configured to engage with the first fastening feature.

Various further embodiments relate to a single use disposable surgical kit including a sterile sealed container including a module configured to fit within the sterile sealed container including surgical instruments housed in a bottom tray including a first fastening feature, and a lid including a second fastening feature congruently aligned with the first fastening feature wherein the first fastening feature is one of a tab portion and a mating slot, the second fastening feature is the other of the tab portion and the mating slot and the second fastening feature is configured to engage with the first fastening feature.

Various additional embodiments are described wherein the second module includes instruments required to fixate a bone fracture. In various embodiments, the module includes a disposable torque limiting screwdriver adapted to engage the fastener heads and further includes a torque limiting stop. The module may additionally include a depth gauge, K-wires, a drill bit and a drill guide.

In various embodiments of the module, the instruments are presented in approximate order of clinical use in a bottom tray. In various embodiments, the bottom tray includes a plurality of cutout areas to house the instruments. In various embodiments, the bottom tray additionally includes a plurality of partitions that allow for the surgical instruments to sit up above the floor of the bottom tray for easier removal during use. The handle and pick-up area of the instruments may be oriented towards the user.

In various embodiments of the module, the bottom tray may include locking tabs diagonally aligned on at least two corners of the tray. In various embodiments, the locking tabs include ridges to facilitate gripping of the tab.

In various embodiments of the module, the bottom tray is covered by a lid, which includes a plurality of cutout areas to enclose the instruments. In various embodiments, the lid may include mating slots present in at least two corners of the lid. Such mating slots may be congruently aligned with the locking tabs included on the tray. In various embodiments, the mating slots may include arm extensions that enclose the locking tab to lock the bottom tray and lid together.

In various embodiments, the first module and the second module may be removable from the sterile sealed container. The sterile sealed container may include cutouts to aid with removal of the first and second modules.

Various embodiments of the kit are described wherein the instruments may be packaged separately from the bone plates, fasteners and fastener housing so that the instrument tray may also be used for an instrument-only sterile kit.

In various embodiments, the sterile container, the first module and the second module, may all be made of a thermoformed plastic material. In various embodiments, the sterile container, the first module and the second module may all be formed from a transparent polymer.

BRIEF DESCRIPTION OF THE DRAWINGS

In order to better understand various exemplary embodiments, reference is made to the accompanying drawings, wherein:

FIG. 2C illustrates a side perspective, detailed view of an embodiment of the locking tab and mating slot configuration.

FIG. 6 illustrates a top perspective view of an embodiment of the fastener housing.

FIG. 6A illustrates a top view of an embodiment of the fastener housing.

FIG. 6B illustrates a front view of an embodiment of the fastener housing showing a plurality of protrusions on the top of the fastener housing and a first and second cavity each including a plurality of stairs, and a plurality of concave depressions that sit on the top surface of the stairs.

FIG. 7 illustrates a top perspective view of an embodiment of the sterile sealed container having a cutout portion to house the second module.

FIG. 7A illustrates a top perspective view of an embodiment of the sterile sealed container having a cutout portion to house the first module.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i e, and/or), unless otherwise indicated (e.g., "or else" or "or in the alternative"). Also, the various embodiments described herein are not necessarily mutually exclusive, as some embodiments can be combined with one or more other embodiments to form new embodiments.

Below embodiments of a disposable single-use sterile kit are described. The kit generally includes a sterile sealed container with cutout portions to house a first and second module. The first module includes a fastener housing and a bone plate and the second module includes instruments required for fixing a bone fracture. The first and second modules are described in more detail in the figures below.

Figure 1:
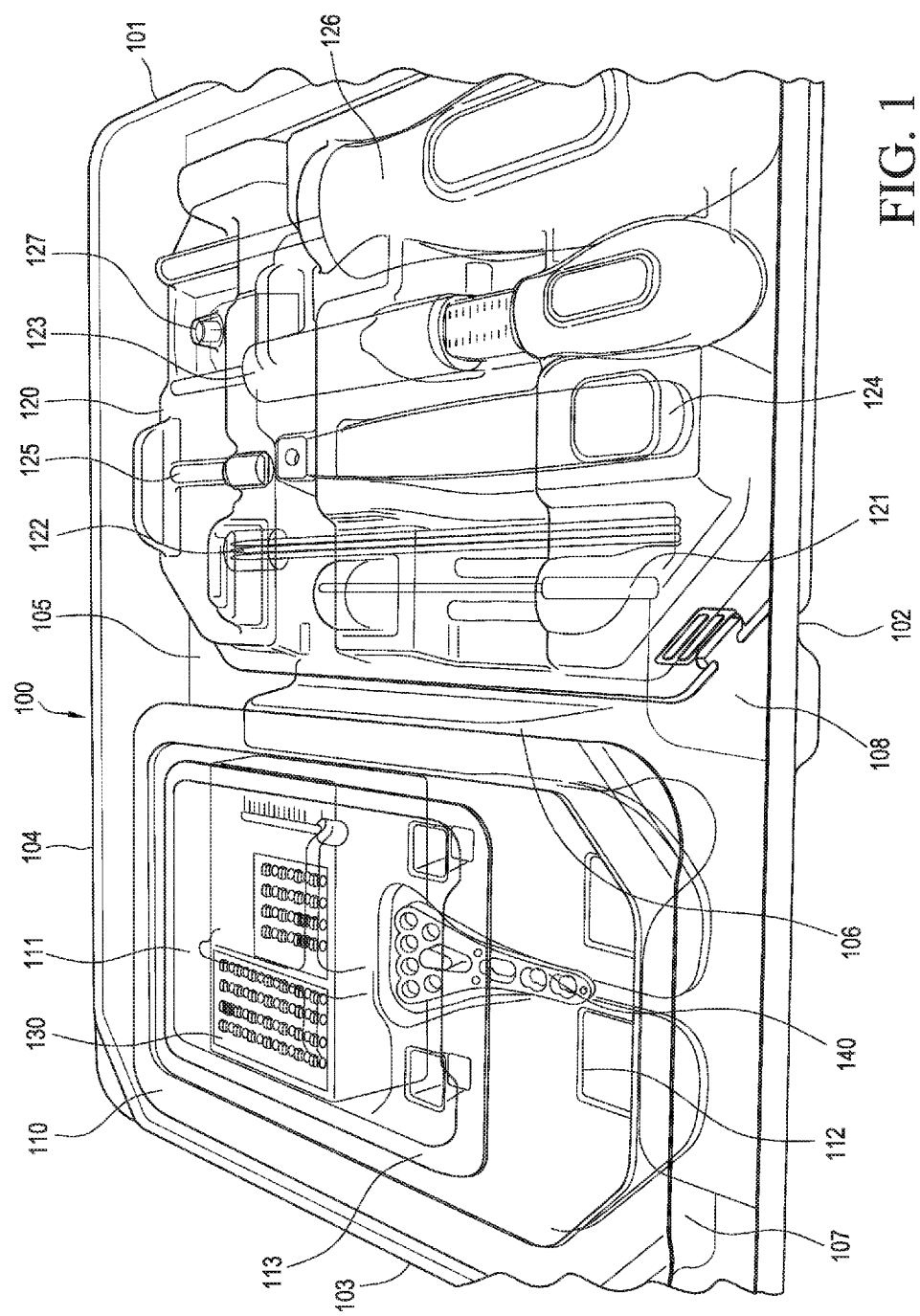
FIG. 1 illustrates a top perspective view of an embodiment of the disposable, single use orthopedic surgical kit showing an embodiment of a sterile container which includes a first module including a bone plate, a fastener housing and a plurality of fasteners and a second module including instruments required to fixate a bone fracture.

FIG. 1 illustrates an embodiment of the sterile kit in an open configuration including a sterile tray 100 with cutout portions to house a first module 110 and a second module 120. The sterile tray 100, first module 110 and second module 120 are thermoformed from any one of a number of polymers, for example polyethylene terephthalate glycol-modified. Sterile tray 100 can have a rectangular shape defined by four tray sides 101-104, although other shapes may be desirable depending on functional, economic, aesthetic or other reasons. Sterile tray 100 includes a tray bottom 105. Sterile tray 100 is compartmentalized by several, integrally formed partitions 106 that may extend from the inside of tray bottom 105 and/or the inside of tray sides 102, 104 to form cutouts 107, 108 where the integrally formed partitions separate the first and second modules from each other. The first module 110 includes wells 111, 112 to house a fastener housing 130 and a bone plate 140. The first module 110 additionally includes a plastic covering 113 that lies on top of the fastener housing 130 and the bone plate 140.

In the embodiment of FIG. 1, the second module 120 includes a drill bit 121, K-wires 122, a depth gauge 123, a variable angle drill guide 124, a coaxial drill guide 125, a torque limiting screwdriver 126 and a torque limiting stop 127.

Figure 2A:
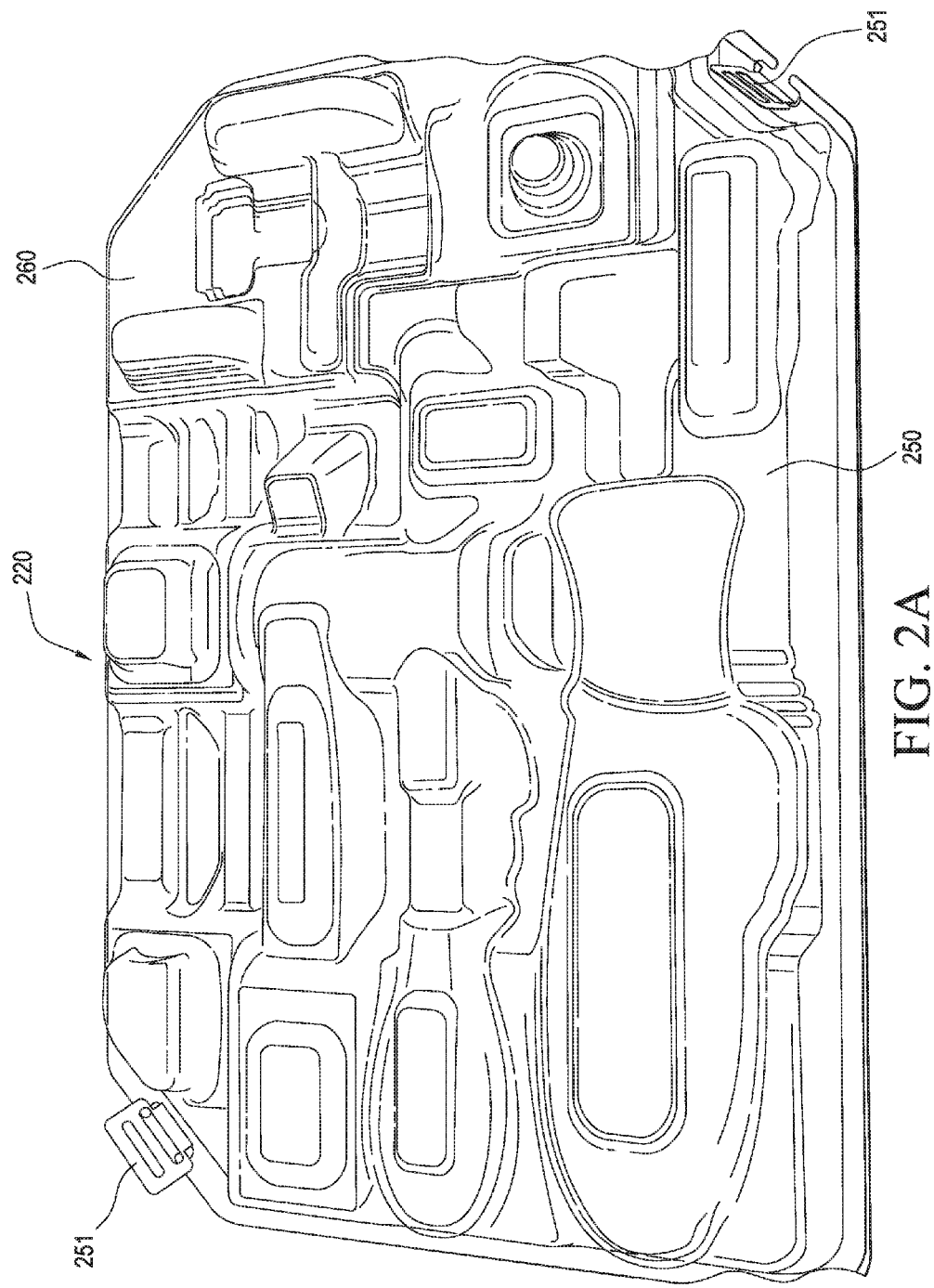
FIG. 2A illustrates a top perspective view of an embodiment of the second module including a bottom tray including locking tabs in the upper right-hand and lower left-hand corners, and a lid covering the bottom tray, wherein the lid includes mating slots in the upper right-hand and lower left-hand corners that align and mate with the locking tabs on the bottom tray. The bottom tray includes cutouts to house the instruments required to fixate a bone fracture. The lid includes cutouts to enclose the instruments.

FIG. 2A illustrates a top perspective view of an embodiment of the second module 220. The second module includes a bottom tray 250 and a lid 260 positioned to sit on top of the bottom tray 250. The bottom tray 250 and lid 260 are locked together using locking tabs 251 positioned diagonally opposite of each other in the upper left-hand corner and lower right-hand corner of the tray 250 as shown. Either one or both of the bottom tray 250 and lid 260 may be formed from a transparent polymer to allow viewing of the components included therein without opening the second module 220.

Figure 2B:
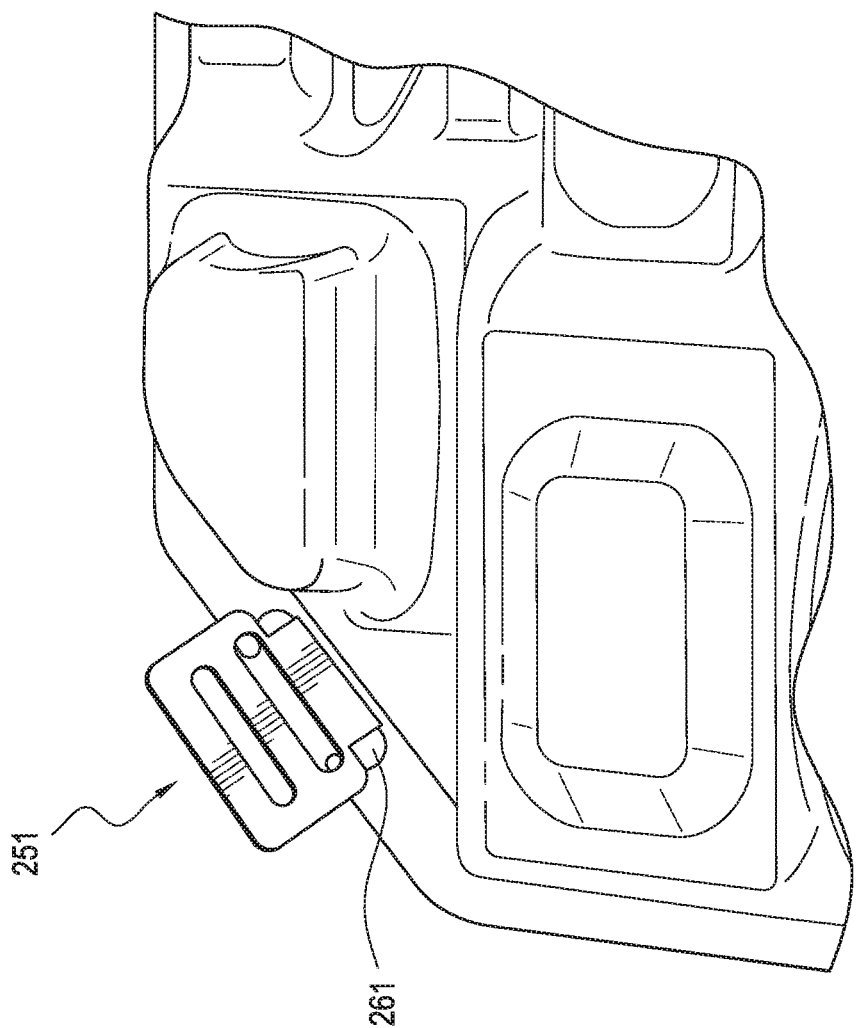
FIG. 2B illustrates a top perspective, detailed view of an embodiment of the locking tab and mating slot configuration.

FIGS. 2B and 2C illustrate a more detailed view of an embodiment of the locking tabs 251. The locking tabs 251 positioned diagonally opposite each other in two corners of the bottom tray 250 lock into mating slots 261 congruently positioned on the lid 260 to receive the locking tabs 251.

Figure 3:
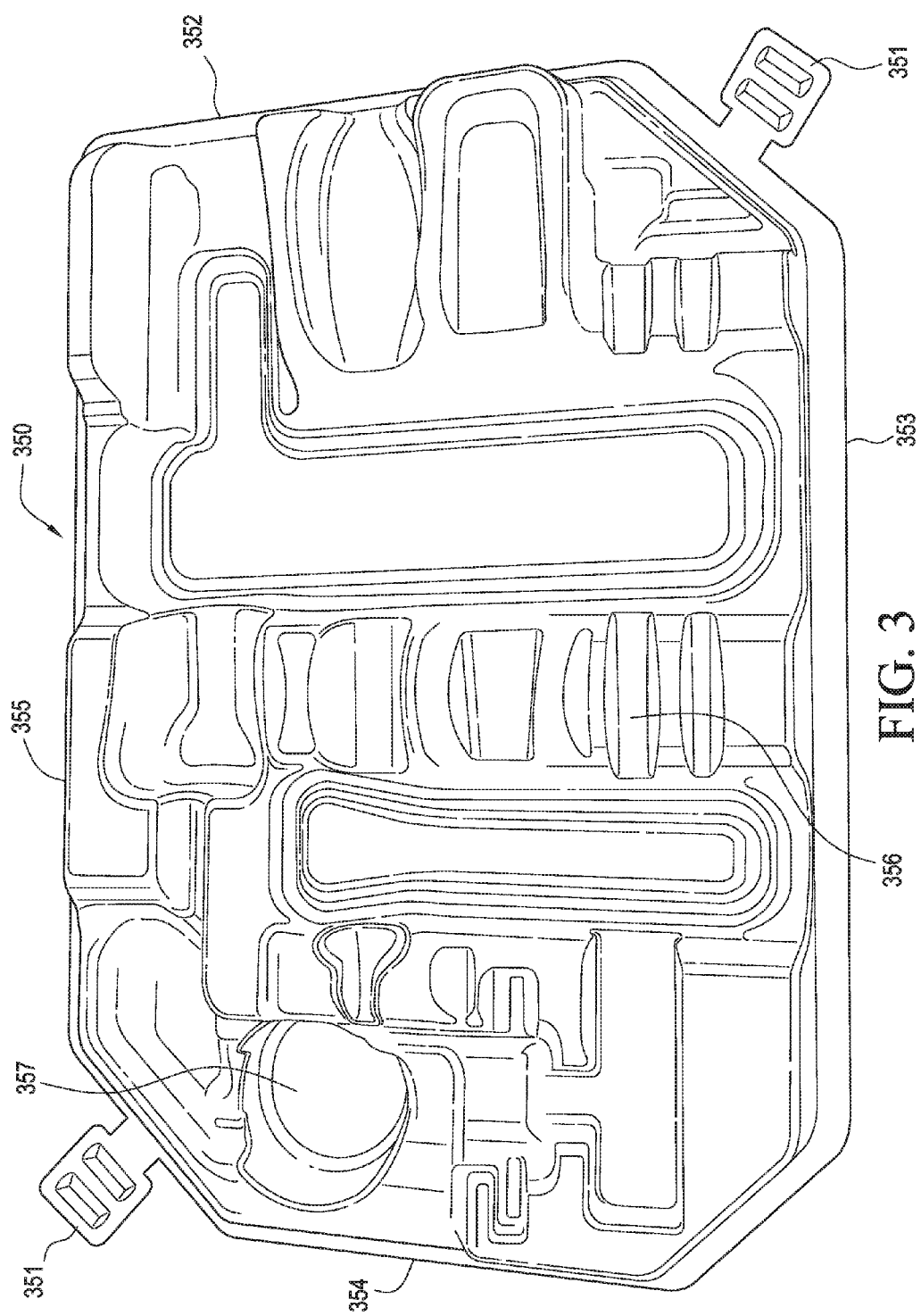
FIG. 3 illustrates a top perspective view of an embodiment of the bottom tray portion of the second module.

FIG. 3 illustrates a top perspective view of an embodiment of the bottom tray 350. The bottom tray 350 can have a generally rectangular shape defined by four tray sides 352-355, although other shapes may be desirable depending on functional, economic, aesthetic or other reasons. Bottom tray 350 is compartmentalized by partitions 356 that form cutout areas 357 in which the instruments required for fixing a bone fracture 121-127 are placed. The partitions 356 are positioned to allow for the instruments 121-127 to sit up above the floor of the bottom tray 350. The bottom tray 350 includes locking tabs 351 diagonally positioned in the upper left-hand corner and lower right-hand corner.

Figure 3A:
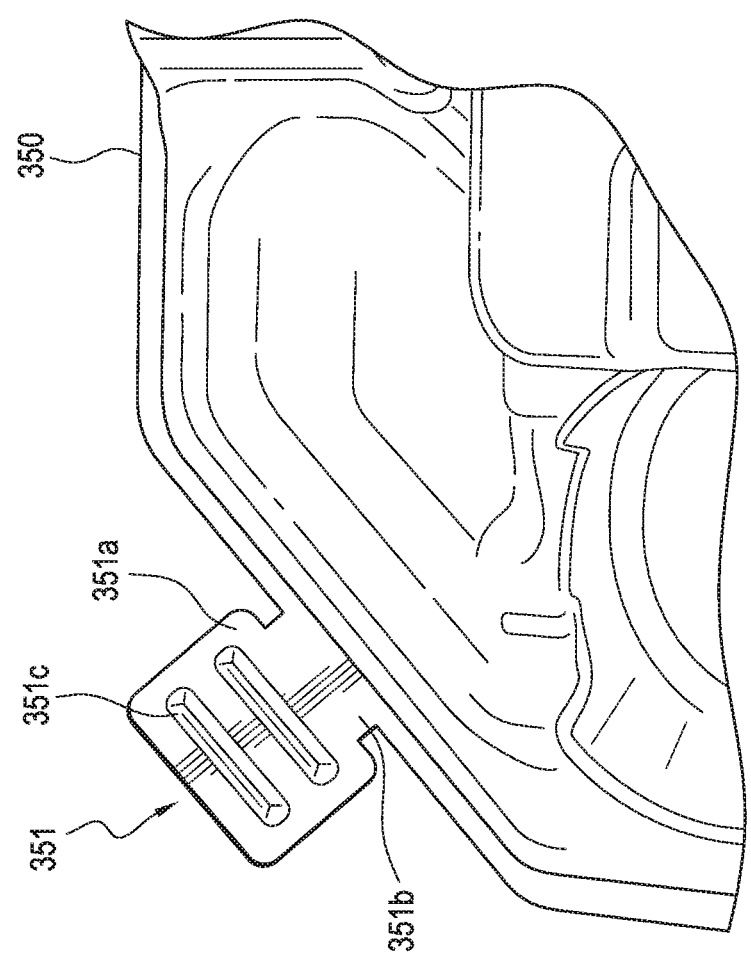
FIG. 3A illustrates a top perspective detailed view of an embodiment of the locking tab included on the bottom tray portion of the second module.

FIG. 3A illustrates a more detailed view of an embodiment of the locking tab 351. The locking tab includes a tab portion 351a which is connected to the bottom tray 350 by way of a connecting piece 351b that is narrower than the tab portion 351a. The tab portion 351a also includes ridges 351c to facilitate gripping of the locking tab 351.

Figure 4:
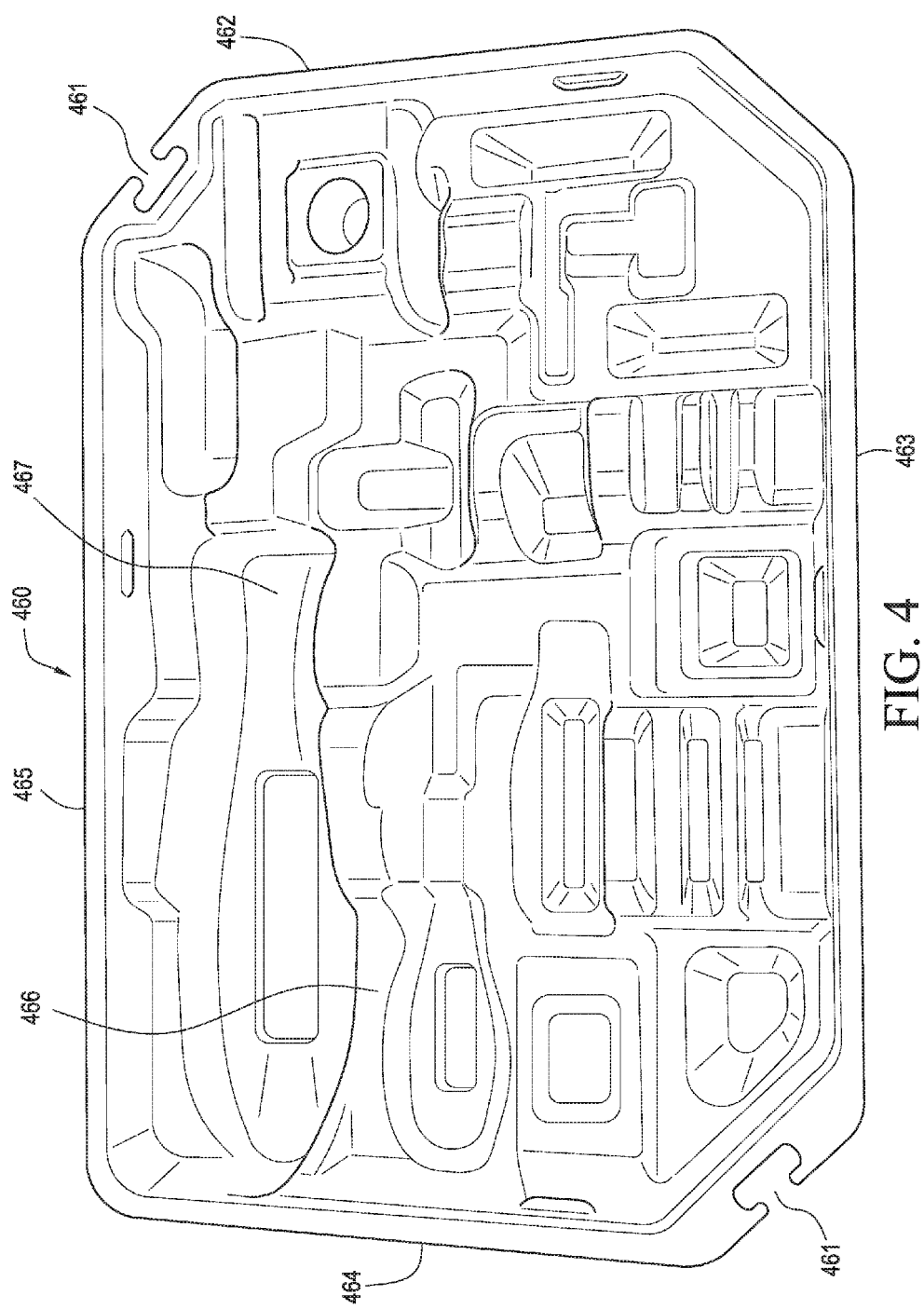
FIG. 4 illustrates a bottom perspective view of an embodiment of the lid portion of the second module showing the instrument cutouts and mating slots.

FIG. 4 illustrates a bottom perspective view of an embodiment of the lid 460. The lid 460 can have a generally rectangular shape defined by four sides 462-465, although other shapes may be desirable depending on functional, economic, aesthetic or other reasons. Lid 460 is compartmentalized by partitions 466 that form cutout areas 467 that fit over the instruments required for fixing a bone fracture 121-127. The lid cutout areas 467 fit together with the bottom tray cutout areas 357 to enclose the individual instruments. The lid 460 includes mating slots 461 in which the locking tabs 351 are inserted to lock the bottom tray 350 and lid 460 together.

Figure 4A:
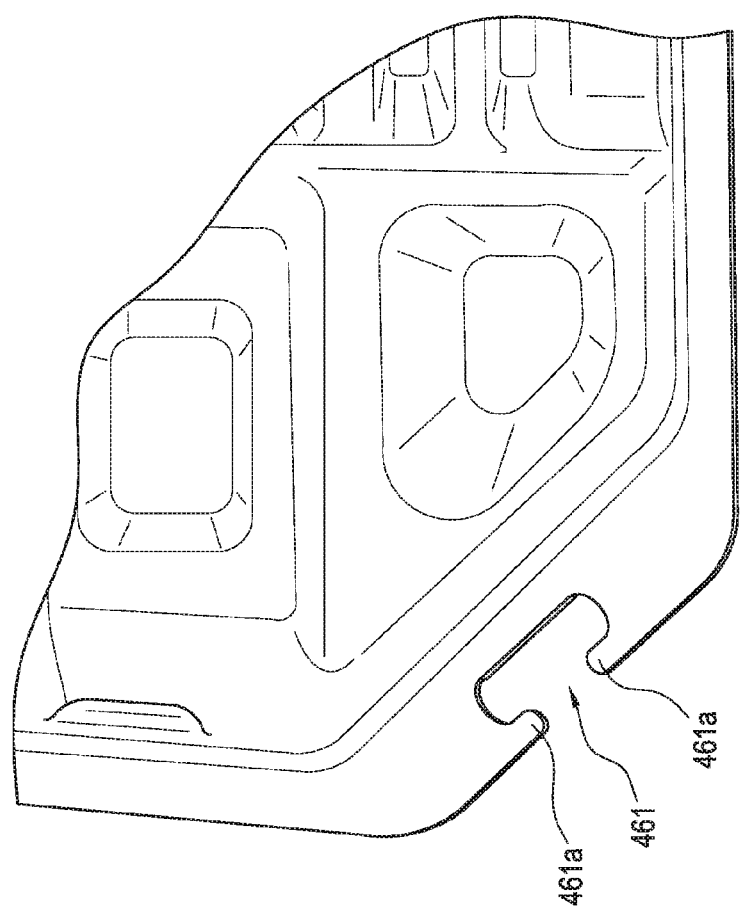
FIG. 4A illustrates a bottom perspective detailed view of an embodiment of the mating slot contained on the lid portion of the second module.

FIG. 4A illustrates a more detailed view of the mating slot 461 which includes arm extensions 461a that enclose the connecting piece 351b and lock the tab portion 351a of the bottom tray 350 within the mating slot 461 of the lid 460.

Figure 5:
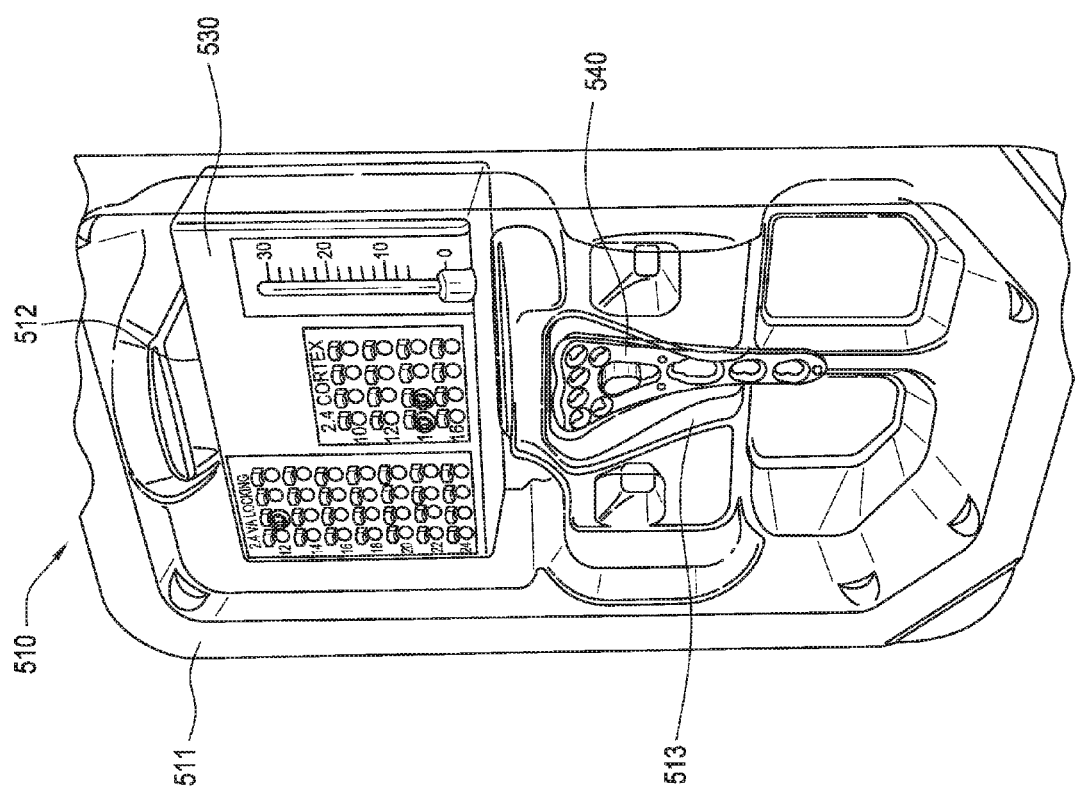
FIG. 5 illustrates a top perspective view of an embodiment of the first module including a tray with wells for a fastener housing and a bone plate. A fastener housing is included in the first well and a bone plate in the second well.

FIG. 5 illustrates a top perspective view of an embodiment of the first module 510. The first module may be in the form of a tray 511 having a generally rectangular shape, although other shapes may be desirable depending on functional, economic, aesthetic or other reasons. The tray 511 includes a first well 512 and a second well 513. The first well 512 includes a fastener housing 530 and the second well 513 includes a bone plate 540.

Figure 6D:
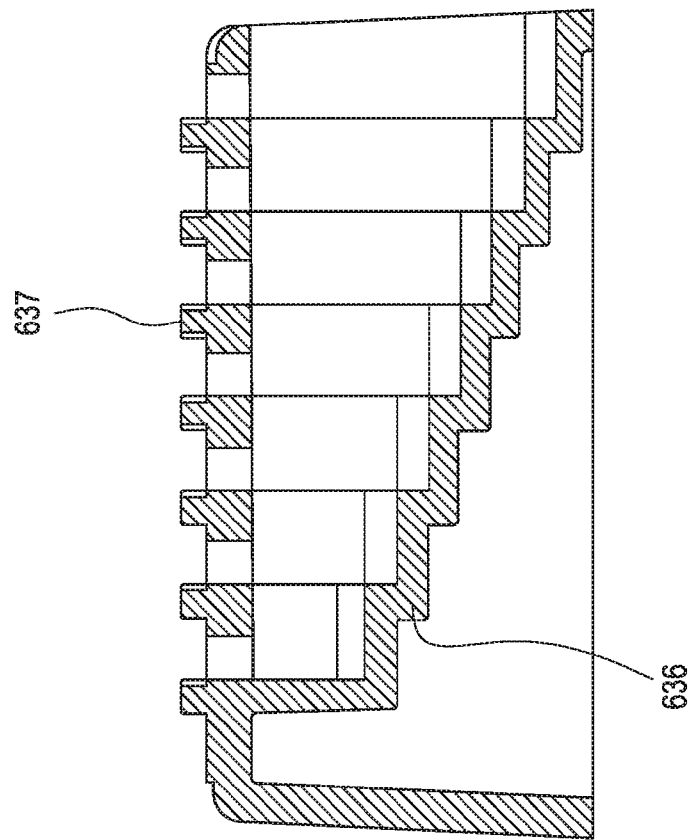
FIG. 6D illustrates a side view of an embodiment of the fastener housing showing a cross-sectional view of the plurality of protrusions included on the top of the fastener housing and the stairs included in the first cavity.
Figure 6C:
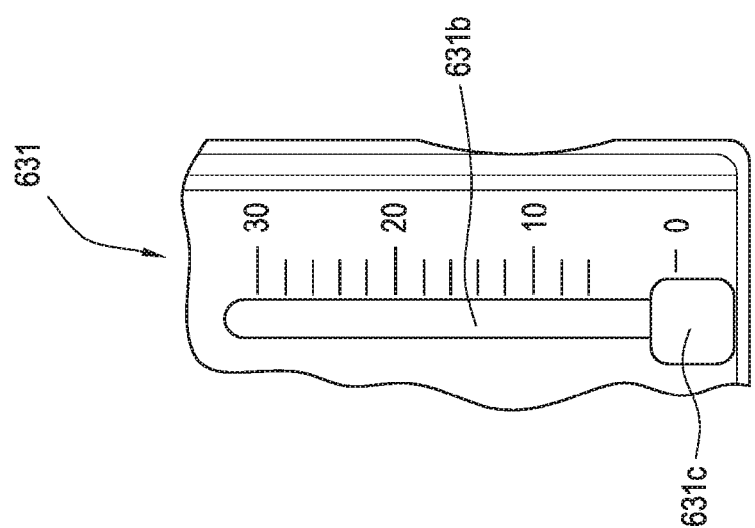
FIG. 6C illustrates a top view of an embodiment of the fastener length gauge included on the top of the fastener housing.

FIG. 6 illustrates a top perspective view of the fastener housing 630. The fastener housing 630 includes a fastener length gauge 631 configured and labeled by a size label 631a for measuring incremental lengths of a plurality of fasteners. The incremental lengths may range, for example, between 10 mm and 30 mm by 2 mm increments. As illustrated in more detail in FIG. 6C, the fastener length gauge 631 has a channel 631b and a seat 631c. Using fastener length gauge 631, the surgeon may quickly confirm the length of a selected fastener prior to implantation of the fastener into the patient, and ensure that the fastener is of sufficient length to properly engage bone, but not so long as to protrude too far from the bone and into soft tissue.

FIGS. 6 and 6A illustrate a perspective and top view of the fastener housing 630 wherein the fastener housing 630 includes a plurality of first fastener receptacles 632 to house a first plurality of fasteners and a plurality of second fastener receptacles 633 to house a second plurality of fasteners. Each of the first and second receptacles 632, 633 is sized and shaped to loosely retain a first plurality of fasteners and a second plurality of fasteners, respectively.

The fastener housing 630 may be prepared using injection-molding to form a first cavity 634 extending from the left sidewall 639a to a molded dividing wall 639b, which is located directly underneath the plurality of first fastener receptacles 632. The fastener housing 630 may further include a second cavity 635 separated from the first cavity by the molded dividing wall 639b, which is located directly underneath the plurality of second fastener receptacles 633. The first cavity 634 and second cavity 635 are surrounded by the molded walls of the fastener housing 630 on three sides with the fourth side open so that the shafts of the fasteners are visible.

As illustrated in FIGS. 6B and 6D, the fastener housing 630 additionally includes a plurality of protrusions 637 that extend upwards and away from the top of the fastener housing 630. The first cavity 634 and the second cavity 635 each include a plurality of stairs 636 that extend downward from the top of the fastener housing, and a plurality of concave depressions 638 that sit on the top surface of the stairs 636. In one embodiment, the heads of the fasteners sit atop the plurality of protrusions 637 while a small portion of the shaft of the fasteners sit within the plurality of concave depressions 638. The stairs 636 cause the fasteners to sit within the fastener housing 630 in a staggered configuration. The plurality of protrusions 637, plurality of stairs 636 and plurality of concave depressions 638 act in combination to prevent fastener angulation or jamming during transit and handling.

The first plurality of fasteners may be arranged in the first fastener receptacle 632 in a plurality of groupings of 7 or fewer fasteners and the second plurality of fasteners may be arranged in the second fastener receptacle 633 in a plurality of groupings of 4 or fewer fasteners. Each grouping corresponds to a particular one of a number of distinct fastener lengths. As shown in FIG. 6, receptacles 632 and receptacles 633 are arranged in groupings, such that each grouping may include up to 4 fasteners of the same shaft length.

When the kit is opened, the user may easily grasp the exposed end of each fastener and remove it from fastener housing 630. Alternately, the user may pick each fastener from the fastener housing 630 using a suitable drive instrument. Since each single-use kit may include only the number of fasteners required for the particular surgical indication, with a few extra, a number of first fastener receptacles 632 and second fastener receptacles 633 may be empty.

FIGS. 7 and 7A illustrate the cutout portions included in sterile tray 700 in which the first module 710 and second module 720 are housed.

It should be appreciated by those skilled in the art that any diagrams or schematic drawings herein represent conceptual views of illustrative structures embodying the principles of the invention.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Further, various elements from the various embodiments may be combined to form other embodiments that are within the spirit and scope of the invention. Accordingly, the foregoing disclosure, description, and figures are for illustrative purposes only and do not in any way limit the invention, which is defined only by the claims.

What is claimed is:

1. A single use disposable surgical kit, comprising:
a sterile sealed container comprising;
a module configured to fit within the sterile sealed container comprising:
surgical instruments housed in a bottom tray comprising a first fastening feature; and
a lid comprising a second fastening feature congruently aligned with the first fastening feature, wherein the first fastening feature is one of a tab portion and a mating slot, the second fastening feature is the other of the tab portion and the mating slot, and the second fastening feature is configured to engage with the first fastening feature.

2. The kit of claim 1, wherein the first fastening feature comprises at least two tab portions positioned diagonally opposite each other in at least two corners of the bottom tray.

3. The kit of claim 1, wherein the second fastening feature comprises at least two mating slots positioned diagonally opposite each other and congruently aligned with the tab portions of the bottom tray.

4. The kit of claim 3, wherein the mating slots include arm extensions that enclose the tab portion to lock the bottom tray and lid together.

5. The kit of claim 2, wherein the tab portions include ridges to facilitate gripping of the tab.

6. The kit of claim 1, wherein the bottom tray includes a plurality of cutout areas to house the surgical instruments.

7. The kit of claim 6, wherein the bottom tray comprises a plurality of partitions that allow for the surgical instruments to sit up above the floor of the tray.

8. The kit of claim 1, wherein the lid contains a plurality of cutout areas to enclose the instruments.

9. The kit of claim 1, wherein the bottom tray and lid are formed from a transparent polymer.

10. The kit of claim 1, wherein the surgical instruments are selected from the group consisting of drill bits, K-wires, depth gauges, drill guides, and screwdrivers, and combinations thereof.

11. A single use disposable surgical kit, comprising:
a sterile sealed container comprising;
a first module configured to fit within the sterile sealed container comprising:
a single bone plate comprising a plurality of fastener apertures; and
a fastener housing;
and
a second module configured to fit within the sterile sealed container comprising:
instruments used to fixate a bone fracture housed in a bottom tray comprising a first fastening feature; and
a lid comprising a second fastening feature congruently aligned with the first fastening feature, wherein the first fastening feature is one of a tab portion and a mating slot, the second fastening feature is the other of the tab portion and the mating slot, and the second fastening feature is configured to engage the first fastening feature to lock the bottom tray and the lid together.

12. The kit of claim 11, wherein the first fastening feature comprises at least two tab portions positioned diagonally opposite each other in at least two corners of the bottom tray.

13. The kit of claim 12, wherein the second fastening feature comprises at least two mating slots positioned diagonally opposite each other and congruently aligned with the tab portions of the bottom tray.

14. The kit of claim 13, wherein the mating slots include arm extensions that enclose the tab portion to lock the bottom tray and lid together.

15. The kit of claim 12, wherein the tab portions include ridges to facilitate gripping of the tab.

16. The kit of claim 11, wherein the bottom tray includes a plurality of cutout areas to house the instruments.

17. The kit of claim 16, wherein the bottom tray comprises a plurality of partitions that allow for the instruments to sit up above the floor of the tray.

18. The kit of claim 11, wherein the lid contains a plurality of cutout areas to enclose the instruments.

19. The kit of claim 11, wherein the bottom tray and lid are formed from a transparent polymer.

20. The kit of claim 11, wherein the instruments are selected from the group consisting of drill bits, K-wires, depth gauges, drill guides, and screwdrivers, and combinations thereof.

21. The kit of claim 11, wherein the fastener housing comprises a plurality of protrusions on the top of the fastener housing, a plurality of stairs extending downward from the top of the fastener housing and a plurality of concave depressions located on the top surface of the plurality of stairs for housing a plurality of fasteners, each of the plurality of fasteners comprising a head and a shaft.

22. The kit of claim 21, wherein the plurality of protrusions extend upward and away from the top of the fastener housing.

23. The kit of claim 21, wherein the plurality of concave depressions are integrally formed on the top surface of the plurality of stairs.

24. The kit of claim 21, wherein the plurality of fasteners sit within the fastener housing in a staggered configuration.

25. The kit of claim 21, wherein the plurality of fasteners are arranged in the fastener housing in a plurality of groupings of fasteners of similar shaft length.

26. The kit of claim 11, wherein the fastener housing further comprises a first fastener receptacle and a second fastener receptacle.

27. The kit of claim 11, wherein the fastener housing further comprises a first cavity that extends from a sidewall of the fastener housing.

28. The kit of claim 27, wherein the plurality of stairs and the plurality of concave depressions are contained within the first cavity.

29. The kit of claim 27, wherein the fastener housing comprises a second cavity that is separated from the first cavity by a dividing wall.

30. The kit of claim 29, wherein the plurality of stairs and the plurality of concave depressions are located within the second cavity.

31. The kit of claim 11, wherein the fastener housing further comprises a fastener length gauge.

32. The kit of claim 11, wherein the fastener housing is an injection molded part.

* * * * *